United States Patent
Olson et al.

(10) Patent No.: US 10,450,340 B2
(45) Date of Patent: Oct. 22, 2019

(54) 3'-DEAMINO-3'-(2''-PYRROLINE-1''-YL)-5-IMINO-13-DEOXYANTHRACYCLINES AND METHODS OF PREPARATION

(71) Applicant: Monopar Therapeutics Inc., Wilmette, IL (US)

(72) Inventors: Richard Olson, Birmingham, AL (US); Gerald Walsh, Birmingham, AL (US)

(73) Assignee: MONOPAR THERAPEUTICS INC., Northbrook, IL (US)

( * ) Notice: Subject to any disclaimer, the term of this patent is extended or adjusted under 35 U.S.C. 154(b) by 251 days.

(21) Appl. No.: 15/434,617

(22) Filed: Feb. 16, 2017

(65) Prior Publication Data

US 2018/0230175 A1   Aug. 16, 2018

(51) Int. Cl.

| | | |
|---|---|---|
| *C07H 15/24* | (2006.01) | |
| *C07H 15/252* | (2006.01) | |
| *C07H 19/04* | (2006.01) | |
| *A61K 31/704* | (2006.01) | |

(52) U.S. Cl.
CPC ......... *C07H 15/252* (2013.01); *A61K 31/704* (2013.01); *C07H 15/24* (2013.01); *C07H 19/04* (2013.01)

(58) Field of Classification Search
None
See application file for complete search history.

(56) References Cited

U.S. PATENT DOCUMENTS

| | | | |
|---|---|---|---|
| 5,942,605 A | 8/1999 | Zhang et al. | |
| 5,948,896 A | 9/1999 | Zhang | |
| 6,184,374 B1 | 2/2001 | Schally et al. | |
| 7,244,829 B2 | 7/2007 | Walsh et al. | |
| 7,776,832 B2* | 8/2010 | Olson | A61K 31/337 514/33 |
| 8,158,591 B2* | 4/2012 | Olson | A61K 31/337 514/33 |

FOREIGN PATENT DOCUMENTS

WO   WO-99/08687 A1   2/1999

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, p. 596.*
Nagy et al., Proc. Natl. Acad. Aci. USA, vol. 93, pp. 2464-2469, Mar. 1996, Medical Sciences.*
Holstein et al., Phase I and pharmacokinetic study of the novel anthracycline derivative 5-imino-13-deoxydoxorubicin (GPX-150) in patients with advanced solid tumors, Invest. New Drugs, 33(3):594-602 (2015).
Jungwirth et al., Regression of rat Dunning R-3327-H prostate carcinoma by treatment with targeted cytotoxic analog of luteinizing hormone-releasing hormone AN-207 containing 2-pyrrolinodoxorubicin, Int. J. Oncol., 10(5):877-84 (1997).
Nagy et al., High yield conversion of doxorubicin to 2-pyrrolinodoxorubicin, an analog 500-1000 times more potent: structure-activity relationship of daunosamine-modified derivatives of doxorubicin, Proc. Natl. Acad. Sci. USA, 93(6):2464-9 (1996).
Stephankova et al., DNA interactions of 2-pyrrolinodoxorubicin, a distinctively more potent daunosamine-modified analogue of doxorubicin, Biochem. Pharmacol., 82(3):227-35 (2011).
Szepeshazi et al., Targeting of cytotoxic somatostatin analog AN-238 to somatostatin receptor subtypes 5 and/or 3 in experimental pancreatic cancers, Clin. Cancer Res., 7(9):2854-61 (2001).

* cited by examiner

*Primary Examiner* — Traviss C McIntosh, III

(74) *Attorney, Agent, or Firm* — Marshall, Gerstein & Borun LLP

(57) ABSTRACT

2-pyrrolino-13-deoxyanthracycline derivatives, medical uses thereof, and a process for making them. A 2-pyrrolino-13-deoxyanthracycline and a 13-deoxyanthracycline can be administered to a patient simultaneously or sequentially in amounts to produce a synergistic therapeutic effect with increased potency and efficacy, compared to the sum of the effects of each drug when administered alone. A composition or preparation of a 2-pyrrolino-13-deoxyanthracycline and a 13-deoxyanthracycline for producing a potent anticancer therapeutic effect is also provided.

20 Claims, No Drawings

3'-DEAMINO-3'-(2"-PYRROLINE-1"-YL)-5-IMINO-13-DEOXYANTHRACYCLINES AND METHODS OF PREPARATION

TECHNICAL FIELD

The present disclosure relates to 13-deoxyanthracyclines, and, more particularly, to 3'-deamino-3'-(2"-pyrroline-1"-yl)-5-imino-13-deoxy anthracyclines and to processes for making and using them. The present disclosure also relates to synergistic combinations of 2-pyrrolino-13-deoxyanthracyclines and 13-deoxyanthracyclines

BACKGROUND OF THE DISCLOSURE

Doxorubicin, an anthracycline antibiotic, is one of the most widely used and very potent anticancer agents. It has a broad spectrum of anticancer activity, being useful in the treatment of acute lymphoblastic leukemia, acute myeloblastic leukemia, Wilms' tumor, neuroblastoma, soft tissue and bone sarcomas, breast carcinoma, ovarian carcinoma, transitional cell bladder carcinoma, thyroid carcinoma, gastric carcinoma, Hodgkin's disease, malignant lymphoma, and bronchogenic carcinoma (doxorubicin package insert, Pfizer Inc., New York, N.Y.). In order to further exploit the enormous tumoricidal potential inherent in the structure of anthracycline antibiotics, thousands of synthetic derivatives have been described, including their analogs linked to various carrier macromolecules.

Nagy et al. (Proc. Natl. Acad. Sci. vol. 93, pp. 2464-2469, 1996) described that modifying doxorubicin (compound I) to 3'-deamino-3'-(2"-pyrroline-1"-yl)doxorubicin (compound II; 2-pyrrolinodoxorubicin) increased the anticancer potency towards human and mouse cancer cells in vitro 500 to 1000 times more than that of doxorubicin.

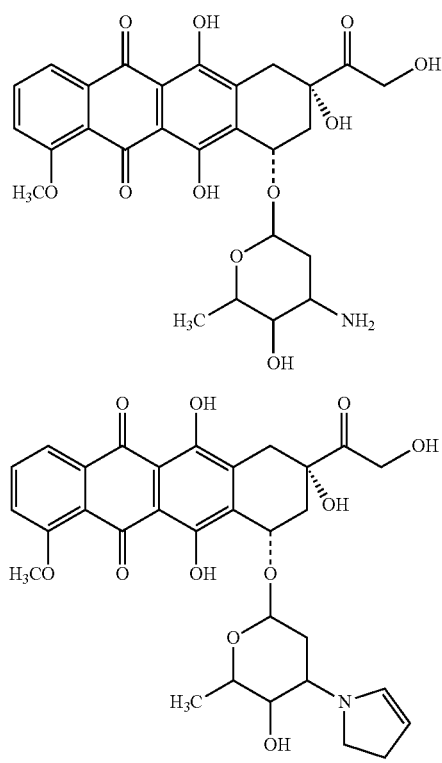

Doxorubicin rapidly enters the nucleus of cells and binds with high affinity to DNA by noncovalent intercalation between base pairs leading to inhibition of synthesis of biomacromolecules. It is generally accepted that biological effects of doxorubicin are associated with its ability to act as a topoisomerase II (topoII) poison perturbing the religation step of this enzyme and forming the ternary doxorubicin-DNA-topoII cleavable complex. 2-pyrrolino-doxorubicin appears to act in the same manner (Stepankova et al., Biochemical Pharmacology 82: 227-235, 2011). There are only small differences in DNA modifications by these anthracyclines and resulting conformational alterations in DNA. Similarly, the ability of 2-pyrrolinodoxorubicin modifications of DNA to inhibit catalytic activity of topoisomerase II does not differ significantly from that of doxorubicin. (Stepankova et al., supra)

However, increasing the potency of doxorubicin by converting it to a 2-pyrrolino compound rendered it nonspecific for cytotoxicity. Consequently, 2-pyrrolinodoxorubicin is toxic or lethal at or below doses that are required for an anticancer effect (Jungwirth, A et al., International Journal of Oncology 10: 877-884, 1997; and Szepeshazi, K et al., Clinical Cancer Research, 7: 2854-2861, 2001). As a result, 2-pyrrolinodoxorubicin has not been useful as a drug to treat cancer. Jungwirth et al., supra and Szepeshazi et al., supra have suggested modifying 2-pyrrolinodoxoubicin by conjugating it at the 14 position OH with somatostatin or luteinizing hormone-releasing hormone analogs. However, these modifications have made the resulting compounds specific for certain tumors, thereby reducing the broad spectrum activity of the parent compound.

SUMMARY OF THE DISCLOSURE

According to the present invention, anthracycline compounds having a 2-pyrrolino moiety are provided that increase the anticancer potency of a broad spectrum while retaining a good safety profile and the broad spectrum feature of the anthracycline. In particular, compounds according to the present invention are represented by the formula X:

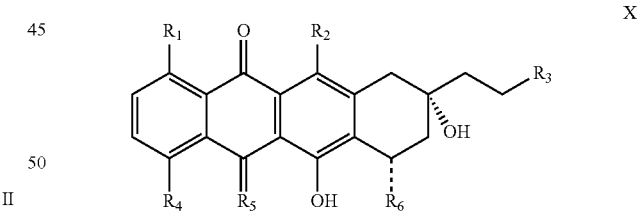

wherein:
each $R_1$, $R_2$, and $R_3$ individually is H or OH;
$R_4$ is selected from the group consisting of H, OH, alkyl, and O-alkyl;
$R_5$ is O or NH; and
$R_6$ is 2-pyrrolino-daunosamine or 2-pyrrolino-epi-daunosamine;
pharmaceutically acceptable salts thereof, deuterated forms thereof, prodrugs thereof, isomers thereof, solvates thereof, and mixtures thereof.

Preferably, the compound is a derivative of an anthracycline selected from the group consisting of 2-pyrrolino-13-deoxydoxorubicin, 2-pyrrolino-13-deoxydaunorubicin, 2-pyrrolino-13-deoxyepirubicin, 2-pyrrolino-13-deoxycarminomycin, and 2-pyrrolino-13-deoxyidarubicin and the 5-imino ($R_5$=NH) analogs thereof.

The present invention is also concerned with a pharmaceutical composition that comprises a compound of formula X, and a pharmaceutically acceptable carrier or excipient.

Another aspect of the present invention relates to a method for suppressing the growth of cells comprises administering to a mammal in need thereof a therapeutically effective amount of a compound of formula X or composition comprising a compound of formula X.

The present invention is further concerned with a therapeutically effective amount of a synergistic combined preparation comprising a first compound and a second compound, wherein: the first compound is a 2-pyrrolino-13-deoxyanthracycline having the formula X:

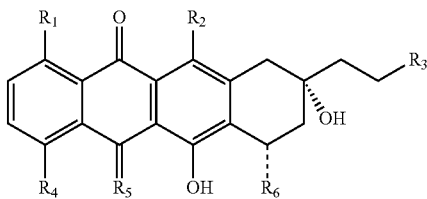

X wherein:
each $R_1$, $R_2$, and $R_3$ individually is H or OH;
$R_4$ is selected from the group consisting of H, OH, alkyl, and O-alkyl;
$R_5$ is O or NH; and
$R_6$ is 2-pyrrolino-daunosamine or 2-pyrrolino-epi-daunosamine;
pharmaceutically acceptable salts thereof, prodrugs thereof, deuterated forms thereof, isomers thereof, solvates thereof, and mixtures thereof; and
the second compound is a 13-deoxyanthracycline, said 13-deoxyanthracycline having the formula:

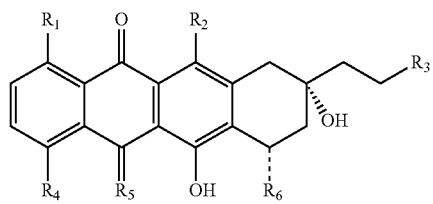

wherein
each of $R_1$, $R_2$ and $R_3$ is independently selected from the group consisting of H and OH;
$R_4$ is selected from the group consisting of H, OH, alkyl, and O-alkyl;
$R_5$ is selected from the group consisting of 0 and NH; and
$R_6$ is a sugar moiety;
pharmaceutically acceptable salts thereof, prodrug thereof, deuterated forms thereof, isomers thereof, solvates thereof, and mixtures thereof;
and
wherein the therapeutically effective amount of the synergistic combined preparation suppresses the growth of cells.

Preferably, the first compound is a derivative of an anthracycline selected from the group consisting of 2-pyrrolino-13-deoxydoxorubicin, 2-pyrrolino-13-deoxydaunorubicin, 2-pyrrolino-13-deoxyepirubicin, 2-pyrrolino-13-deoxycarminomycin, and 2-pyrrolino-13-deoxyidarubicin and the 5-imino analogs thereof and the second compound is a derivative of an anthracycline selected from the group consisting of 13-deoxydoxorubicin, 13-deoxydaunorubicin, 13-deoxyepirubicin, 13-deoxycarminomycin, 13-deoxyidarubicin, 13-deoxyannamycin, and 13-deoxyamrubicin and the 5-imino analogs thereof.

A still further aspect of the present invention is a pharmaceutical composition that comprises the synergistic combined preparation disclosed hereinabove and a pharmaceutically acceptable carrier or excipient.

The present invention is also concerned with a method for suppressing the growth of cells with a synergistic combined preparation of the first compound as defined above and the second compound as defined above, comprising administering to a mammal in need thereof a therapeutically effective amount of the synergistic combined preparation, pharmaceutically acceptable salts thereof, deuterated forms thereof, prodrugs thereof, isomers thereof, or solvates thereof.

The synergistic combined preparation can be formulated and administered wherein the second compound is present in an amount that is lower than its therapeutically effective amount. The synergistic combined preparation can also be formulated and administered wherein the first compound is present in an amount that is lower than its therapeutically effective amount. By way of example, when the second compound is present in an amount that is lower than its therapeutically effective amount the weight ratio of the second compound to the first component typically can be about 0.005 to about 0.10:1 and more typically about 0.01 to about 0.10:1. Also, by way of example, when the first compound is present in an amount that is lower than its therapeutically effective amount the weight ratio of the first compound to the second component typically can be about 0.005 to about 0.10:1 and more typically about 0.01 to about 0.10:1.

Still other objects and advantages of the present disclosure will become readily apparent by those skilled in the art from the following detailed description, wherein it is shown and described only the preferred embodiments, simply by way of illustration of the best mode. As will be realized, the disclosure is capable of other and different embodiments, and its several details are capable of modifications in various obvious respects, without departing from the disclosure. Accordingly, the description is to be regarded as illustrative in nature and not as restrictive.

DETAILED DESCRIPTION OF THE INVENTION

While the following description details certain embodiments of the present disclosure, it is to be understood that the disclosure is not limited in its application to the details of compositions and combinations of the compounds described in the accompanying examples and experiments, since the disclosure is capable of other embodiments and of being practiced in various ways.

The 2-pyrrolino-13-deoxy anthracycline compounds employed according to the present disclosure have the following formula X:

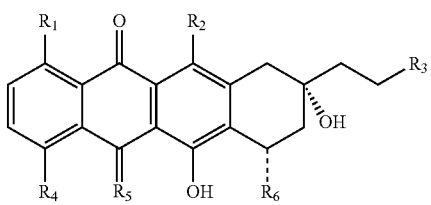

wherein each $R_1$, $R_2$, and $R_3$ individually is H or OH; $R_4$ is selected from the group consisting of H, OH, alkyl, and O-alkyl; $R_5$ is O or NH; and $R_6$ is 2-pyrrolino-daunosamine or 2-pyrrolino-epidaunosamine. The more typical 2-pyrrolino-13-deoxyanthracyclines are 2-pyrrolino-13-deoxydoxorubicin, 2-pyrrolino-13-deoxydaunorubicin, 2-pyrrolino-13-deoxyepirubicin, 2-pyrrolino-13-deoxycarminomycin, and 2-pyrrolino-13-deoxyidarubicin and the 5-imino analogs thereof ($R_5$=NH).

The alkyl groups typically contain 1 to 6 carbon atoms and can be straight or branch chained. Examples of suitable alkyl groups include methyl, ethyl, i-propyl, n-propyl, butyl, n-butyl, pentyl and hexyl.

Pharmaceutically acceptable salts" refer to derivatives of the disclosed compounds wherein the parent compound is modified by making acid salts thereof. The compounds of this disclosure form acid addition salts with a wide variety of organic and inorganic acids and includes the physiologically acceptable salts which are often used in pharmaceutical chemistry. Such salts are also part of this disclosure. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkonic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromobenzenesulfonate, chlorobenzenesulfonate, ethanesulfonate, 2-hydroxyethanesulfonate, methanesulfonate, naphthalene-1-sulfonate, naphthalene-2-sulfonate, p-toleunesulfonate, xylenesulfonate, tartarate, and the like.

The deuterated forms contain heavy hydrogen including deuterium and/or tritium.

It is understood that the compounds of the present disclosure relate to all optical isomers and stereo-isomers at the various possible atoms of the molecule, unless specified otherwise.

"Solvates" refers to the compound formed by the interaction of a solvent and a solute and includes hydrates. Solvates are usually crystalline solid adducts containing solvent molecules within the crystal structure, in either stoichiometric or nonstoichiometric proportions.

Prodrug forms of the compounds bearing various nitrogen functions (amino) may include the following types of derivatives where each R group individually may be hydrogen, substituted or unsubstituted alkyl, aryl, alkenyl, alkynyl, heterocycle, alkylaryl, aralkyl, aralkenyl, aralkynyl, cycloalkyl or cycloalkenyl groups.

(a) Carboxamides, —NHC(O)R
(b) Carbamates, —NHC(O)OR
(c) (Acyloxy)alkyl Carbamates, NHC(O)OROC(O)R
(d) Enamines, —NHCR(=CHCO2R) or —NHCR(=CHCONR2)
(e) Schiff Bases, —N=CR2.

The synthesis and purification of 13-deoxyanthracyclines are disclosed in U.S. Pat. Nos. 5,942,605; 5,948,896; and 7,244,829, which are incorporated herein by reference. The process of converting anthracyclines to 2-pyrrolino-anthracyclines is disclosed in Nagy et al., supra and in U.S. Pat. No. 6,184,374, which are incorporated herein by reference.

It has been discovered that the 13-deoxy forms of doxorubicin, daunorubicin, or other similar anthracyclines will not be metabolically converted to cardiotoxic 13-dihydro forms, and are, therefore, devoid of cumulative irreversible cardiotoxicity. In particular, see WO99/08687, U.S. Pat. Nos. 5,948,896 and 5,942,605 and PCT/US99/04704, disclosures of which are incorporated herein by reference.

5-imino-13-deoxydoxorubicin has been tested in a Phase I clinical trial in patients with advanced tumors (Holstein, SA Investigative New Drugs. 2015, 33: 594-602). This compound had anticancer activity in a variety of carcinomas, sarcomas, and bladder cancer. In addition, the compound was well tolerated with relatively mild toxicity for an anthracycline. Heretofore it has been unknown whether such 13-deoxyanthracyline anticancer agents would have an enhanced anticancer effect if converted to 2-pyrrolino analogs and at the same time have an acceptable safety profile. As noted above, 2-pyrrolino-doxorubicin is very potent but also toxic and lethal at or near doses that are required to have anticancer efficacy.

2-pyrrolino-13-deoxyanthracyclines of formula X exhibit anticancer, antitumor, and/or neoplastic efficacy, that are useful for all types of therapies for treating cancers, neoplasms, or tumors, including leukemia, melanoma, liver, breast, ovary, prostate, stomach, pancreas, lung, kidney, colon, and central nervous system tumors. The treatments of the present disclosure provide methods of suppressing the growth of normal cells (such as psoriatic skin cells), cancers, tumors, and neoplasms in mammals, including humans, with compounds of formula X.

A pharmaceutical composition of the present disclosure comprises a compound or compounds of formula X, pharmaceutically acceptable salts thereof, deuterated forms thereof, prodrug thereof, isomers thereof, and/or solvates thereof in a pharmaceutically acceptable carrier or excipient. These pharmaceutical compositions of the present disclosure are useful in anticancer therapy and treating cell proliferative disorders. The pharmaceutically acceptable carriers or excipients are well known to those having ordinary skill in the art of formulating compounds in a form of pharmaceutical compositions, combinations, mixtures, and preparations. A pharmaceutically acceptable carrier refers to one or more compatible solid or liquid filler, diluent, or encapsulating substances which are suitable for administration to mammals including humans. Pharmaceutical compositions, combinations, mixtures, and preparations suitable for parenteral administration are formulated in a sterile form which may be a sterile solution or suspension in an acceptable diluent or solvent.

The amount of an active ingredient contained in the pharmaceutical composition may vary quite widely depending on many factors, such as the route of administration and the vehicle. In the present invention, a pharmaceutical composition may contain from about 0.1 to 1000 mg of a 2-pyrrolino-13-deoxy anthracycline of formula X per ml or gram of pharmaceutical formulation.

In a method of use, a 2-pyrrolino-13-deoxy anthracycline of formula X, pharmaceutically acceptable salts thereof, deuterated forms thereof, prodrug thereof, isomers thereof, and/or solvates thereof is administered to a patient in need thereof at a dose from about 0.1 mg/m$^2$ body surface area to about 1000 mg/m$^2$ body surface area, more typically from about 10 mg/m$^2$ body surface area to about 500 mg/m$^2$ body surface area. The doses of the 2-pyrrolino-13-deoxy anthracyclines can be administered as frequently as necessary. The actual method of administration will vary according to the particular formulation, composition, combination, mixture, or preparation, the particular cancer or proliferative cell disorder being treated, and the particular patient being treated.

The composition can be administered to a patient in any manner that is medically acceptable, including orally, parenterally, topically, or by implantation. Oral administration includes administering the composition in the form of tablets, capsules, lozenges, suspensions, solutions, emulsions, powders, syrups, and the like. The preferred route of administration is parenteral.

The actual method and order of administration may vary according to the particular pharmaceutical formulation of the compound of formula X being utilized, the particular cancer being treated, the severity of the disease state being treated, and the particular patient being treated. The dosage ranges for the administration of the constituents may vary with the age, condition, sex, and extent of the disease in the patient, and can be determined by one of ordinary skill in the art.

Examples of cancers treated according to the present invention include breast cancer, bladder cancer, Karpi's sarcoma, leukemia such as acute lymphoblastic leukemia and acute myeloblastic leukemia, Wilm's tumor, neuroblastoma, lymphoma, soft tissue and bone sarcomas, ovarian cancer, bladder cancer including transitional cell bladder cancer, thyroid cancer, gastric carcinoma, Hodgkin's disease and bronchogenic carcinoma.

To test whether a 13-deoxy anthracycline could be converted to a 2-pyrrolino-13-deoxy anthracycline, the method of Nagy et al., supra was used to convert the amine on the sugar to a 3'-deamino-3'-(2"-pyrroline-1"-yl) moiety. As an example, 5-imino-13-deoxydoxorubicin III was converted to 2-pyrrolino-5-imino-13-deoxydoxorubicin IV. Compound IV was tested in vitro and in vivo for anticancer activity and potency. The conversion of compound III to compound IV is shown below:

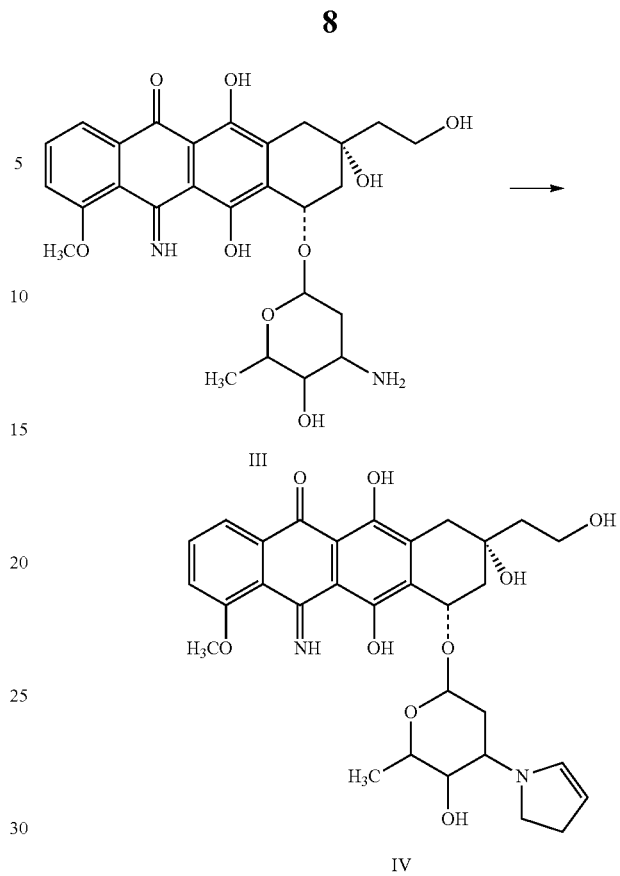

The conversion of a 13-deoxy anthracycline to a 2-pyrrolino-13-deoxy anthracycline of formula X with improved potency and efficacy is shown, by way of example, in the following synthesis and biological tests, which are intended to illustrate but not to limit the present disclosure.

Example 1

5-imino-13-deoxydoxorubicin HCl salt (III, 62.4 mg, 0.1104 mmol) was dissolved in 10 ml of dimethylformamide (DMF) and 90 ml dichloromethane in a flask. The flask was purged with nitrogen, and then 4-iodobutyraldehyde (0.697 g, 3.535 mmol, 33 equivalents) in 10 ml dichloromethane was added dropwise. Next, N,N-diisopropylethylamine (0.152 g, 205 µL, 1.178 mmol, 11 equivalents) was added via a syringe, and the reaction flask was wrapped in foil and allowed to stir for 1.25 hour at room temperature. After the reaction was complete, as measured by high pressure liquid chromatography (HPLC), 20 mL of 1% trifluoroacetic acid (TFA) in methanol was added. The solution was concentrated via rotatory evaporation to ¼ its original volume. An ether/hexane solution (1:5, 100 ml) was added at which time a deep purple precipitate formed. The solid was allowed to settle and the light purple mother liquor was decanted by cannula. The remaining solid was washed with an additional volume of 1:5 ether/hexane and then dried overnight under high vacuum in an aluminum foil wrapped flask. The yield of 2-pyrrolino-5-imino-13-deoxydoxorubicin IV was 61.0 mg (0.0878 mmol, 79.5%) as a purple powder that was 92% pure, as measured by HPLC.

Example 2

The growth inhibitory potency of 2-pyrrolino-5-imino-13-deoxydoxorubicin IV, 5-imino-13-deoxydoxorubicin III, and doxorubicin I against several cancer cell lines was evaluated using the resazurin fluorescence assay. The growth inhibitory potency was measured as the inhibitory concentration of a compound required to inhibit cell growth by 50% ($IC_{50}$). The cancer cells were seeded into 96-well plates ($0.5-1\times10^4$ cells/well) with appropriate media, incubated with drug for 48 hours, and then treated with resazurin (final concentration, 0.01%), a non-fluorescent blue dye, for 24 hours. The fluorescence (Ex560 nm/Em590 nm) was recorded using a BioTek SynergyHT multiwell plate fluorimeter. Healthy cells metabolize resazurin to resorufin, a fluorescent pink dye. Thus, fluorescence is a proxy for cell viability and used to determine the effect of cytotoxic agents on cell cultures. The results of cytotoxic activity assays in five human cancer cell lines and one normal human cell line are summarized in Table 1. Against all cancer cells, 2-pyrrolino-5-imino-13-deoxydoxorubicin IV was significantly more potent than the parent compound 5-imino-13-deoxydoxorubicin III, with $IC_{50}$ values that were 13 to 27 times lower than those of 5-imino-13-deoxydoxorubicin III. The activity of 2-pyrrolino-5-imino-13-deoxydoxorubicin IV was also greater than that of doxorubicin I, with $IC_{50}$ values that were, on average, lower than those of doxorubicin I.

The compounds were also tested against a normal non-cancer cell line, normal human fibroblasts (HADF). 2-pyrrolino-5-imino-13-deoxydoxorubicin IV was half as cytotoxic (39.75/18.9) than doxorubicin I against HADF (normal) cells. The results of these studies are shown in Table 1.

The compounds were further tested against a uterine fibrosarcoma cell line, MES-SA, sensitive to doxorubicin (compound I), and against a uterine fibrosarcoma cell line MES-SA/MX2 resistant to doxorubicin. These results are shown in Table 2.

TABLE 1

Antiproliferative activity ($IC_{50}$) of Compound IV, Compound III, and Compound I against human cancer cell lines and a normal cell line using the resazurin assay. $IC_{50}$ values are the mean (±SEM) from 3 separate assays, each performed in triplicate.

| Cell Line | Cell Type | Drug $IC_{50}$ Values (µM) | | |
|---|---|---|---|---|
| | | Compound IV | Compound III | Compound I |
| SW-872 | Liposarcoma | 0.57 ± 0.23 | 7.38 ± 0.45 | 33.7 ± 7.5 |
| RD | Rhabdomyosarcoma | 0.44 ± 0.13 | 11.89 ± 3.99 | 0.43 ± 0.15 |
| GCT | Histiocytoma | 0.175 ± 0.015 | 3.37 ± 0.35 | 0.279 ± 0.036 |
| HeLa | Cervical Adenocarcinoma | 0.467 ± 0.104 | 9.82 ± 0.93 | 0.605 ± 0.095 |
| T47D | Breast Ductal Carcinoma | 0.817 ± 0.561 | 18 ± 13.7 | 10.3 ± 7.8 |
| | Average | 0.49 | 10.09 | 9.06 |
| HADF | Human Adult Dermal Fibroblasts | 39.75 | 58.9 | 18.9 |

Compound IV is shown to be, on average, 20 (10.09/0.49) times more potent than compound III for inhibiting cell growth of cancer cells and 18 (9.06/0.49) times more potent than compound I. Compound IV, on average, is 81 (39.75/0.49) times more potent against cancer cells than a normal non-cancer cell line. Compound III, on average, is only 5.8 (58.9/10.09) times more potent against cancer cells than a normal type cell and compound I is only 2 (18.9/9.06) times more potent. Thus, the selectivity of compound IV for cancer cells versus normal cells is shown to be 14 (81/5.8) times greater compared to compound III and 40 (81/2) times greater compared to compound I. This result was unanticipated and is in marked contrast to that reported for compound II (2-pyrrolinodoxorubicin) which has little or no selectivity for cancer cells versus normal cells. Even more unexpected and not predicted was that the selectivity of compound IV for cancer cells versus normal cells is shown to be 40 times greater compared to compound I (doxorubicin). Thus, forming a 2-pyrrolino analog of 5-imino-13-deoxydoxorubicin (III) produced a more potent and safer anthracycline compared to forming a 2-pyrrolino analog of doxorubicin (I) which resulted in highly potent toxin II with no useful therapeutic utility.

TABLE 2

Antiproliferative activity ($IC_{50}$) of Compound IV, Compound III, and Compound I against human cancer cell lines sensitive and resistant to doxorubicin. $IC_{50}$ values are the mean (±SEM) from 3 separate assays, each performed in triplicate.

| Cell Line | Cell Type | Drug $IC_{50}$ Values (µM) | | |
|---|---|---|---|---|
| | | Compound IV | Compound III | Compound I |
| MES-SA | Uterine fibrosarcoma (sensitive) | 0.76 ± 0.16 | 10.5 ± 1.0 | 0.55 ± 0.08 |
| MES-SA/MX2 | Uterine fibrosarcoma (resistant) | 0.66 ± 0.003 | 90 | 7.8 ± 1.8 |

Compound IV is more potent than compound III and about equal in potency to compound I in the doxorubicin sensitive fibrosarcoma strain. In the resistant fibrosarcoma strain compound I is 14 (7.8/0.55) times less potent than in the sensitive fibrosarcoma strain, as is expected. On the other hand, compound IV is about equal in potency in the resistant fibrosarcoma strain compared to the sensitive fibrosarcoma strain. Thus, compound IV is 12 times more potent than compound I in an anthracycline resistant cell line, indicating that, in the treatment of cancer, the cancer tissue will not become resistant to compound IV. This feature represents a significant improvement in compound IV over compounds III and I.

Example 3

To assess in vivo drug activity against a primary tumor growth model of sarcoma, an experiment was conducted using commercially available human HT1080 fibrosarcoma cells engineered to express luciferase (HT1080-luc; PerkinElmer). The inhibitory potency of Compound III and Compound IV against HT1080-luc was measured in vitro by the methods described in Example 2. The $IC_{50}$±SEM (µM) for compound IV was 3.51±1.79 and for compound III was 10.0±6.1. HT1080-luc tumors were initiated in 6 week old female SCID mice (Harlan) by orthotopic subcutaneous injection of $1\times10^6$ cells in each flank. After allowing the tumors to establish for 6 days, mice were randomized to one of three treatment groups and treated three times per week by intraperitoneal injection with compound IV or compound III, 2.4 mg/kg in physiological buffered saline (PBS), or vehicle (PBS). Results are shown in Table 3. Based on in vivo bioluminescent imaging results, tumor progression was reduced significantly statistically at day 20 in mice treated with compound IV relative to those receiving PBS-only treatment. Tumor progression was not significantly reduced with compound III. At day 20 tumor weight was reduced 53% with compound IV while reduced only 36% with compound III at the same given dose. These results indicate an increased efficacy of compound IV versus compound III at a given dose and are consistent with the in vitro results presented above. Compound IV was well tolerated by the mice with no deaths and no overt signs of toxicity such as ptosis, lordosis, lethargy, and weight loss. This is in contrast to 2-pyrrolinodoxorubicin which can be lethal at its effective dose range.

TABLE 3

Average tumor weights at day 20.

| Treatment: | Averge tumor weight (g) | SEM |
| --- | --- | --- |
| PBS | 2.18 | ±0.48 |
| Compound III (2.4 mg/kg) | 1.40 | ±0.30 |
| Compound IV (2.4 mg/kg) | 1.03* | ±0.21 |

Asterisk *indicates significant decrease from PBS treatment controls (p < 0.05).
Values are means ± standard error of the mean.

The anti-cell proliferative therapeutic effects of 2-pyrrolino-13-deoxyanthracyclines of formula X are significantly increased by combining them with 13-deoxyanthracyclines of formula Y. This increased therapeutic effect is a result of an unexpected synergism between 2-pyrrolino-13-deoxyanthracyclines and 13-deoxyanthracyclines. The 13-deoxyanthracycline compounds employed according to the present disclosure have the following formula Y:

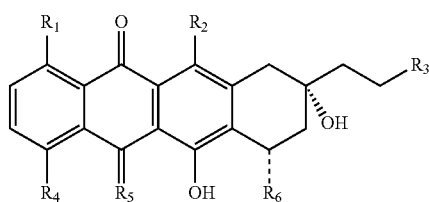

Y wherein each $R_1$, $R_2$, and $R_3$ individually is H or OH; $R_4$ is selected from the group consisting of H, OH, alkyl, and O-alkyl; $R_5$ is O or NH; and $R_6$ is sugar having a primary amine group or no amine group; pharmaceutically acceptable salts thereof, deuterated forms thereof, prodrug thereof, isomers thereof, and/or solvates thereof. The more typical 13-deoxyanthracyclines are 13-deoxydoxorubicin, 13-deoxydaunorubicin, 13-deoxyepirubicin, 13-deoxycarminomycin, 13-deoxyidarubicin, 13-deoxyannamycin, and 13-deoxyamrubicin and the 5-imino analogs thereof ($R_5$=NH).

The alkyl group in the above formula Y is the same as disclosed hereinabove.

In addition, the treatment of the present disclosure employing the combination of 2-pyrrolino-13-deoxyanthracyclines and 13-deoxy anthracyclines, exhibits anticancer, antitumor, and/or neoplastic efficacy, that are useful for all types of therapies for treating cell proliferative disorders such as inflammation, psoriasis, cancers, neoplasms, or tumors, including leukemia, melanoma, liver, breast, ovary, prostate, stomach, pancreas, lung, kidney, colon, and central nervous system tumors. The treatment of the present disclosure provides a method of suppressing the growth of cancers, tumors, neoplasms, and normal cells in mammals, including humans.

A typical composition, combination, mixture, or preparation of the constituents according to the disclosure is a compound of formula X, pharmaceutically acceptable salt thereof, deuterated form thereof, prodrug thereof, isomer thereof, and/or solvate thereof combined with a compound of formula Y; pharmaceutically acceptable salt thereof, deuterated form thereof, prodrug thereof, isomer thereof, and/or solvate thereof. A more typical composition, combination, mixture, or preparation is a 2-pyrrolino-13-deoxyanthracycline selected from the group consisting of 2-pyrrolino-13-deoxydoxorubicin, 2-pyrrolino-13-deoxydaunorubicin, 2-pyrrolino-13-deoxyepirubicin, 2-pyrrolino-13-deoxycarminomycin, and 2-pyrrolino-13-deoxyidarubicin and the 5-imino analogs thereof; pharmaceutically acceptable salt thereof, deuterated form thereof, prodrug thereof, isomer thereof, and/or solvate thereof and a 13-deoxyanthracycline selected from the group consisting of 13-deoxydoxorubicin, 13-deoxydaunorubicin, 13-deoxyepirubicin, 13-deoxyidarubicin, 13-deoxyannamycin, 13-deoxycarminomycin, 13-deoxyamrubicin and the 5-imino analogs thereof; pharmaceutically acceptable salt thereof, deuterated form thereof, prodrug thereof, isomer thereof, and/or solvate thereof.

The constituents of the composition, combination, mixture, or preparation can be administered to a patient simultaneously, separately, sequentially, or consecutively. The constituents can be administered to a patient in any acceptable manner that is medically acceptable, including orally, parenterally, topically, or by implantation. Oral administration includes administering the constituents of the compositions, combinations, mixtures, or preparations in the form of tablets, capsules, lozenges, suspensions, solutions, emulsions, powders, syrups, and the like. The preferred route of administration is parenteral.

The actual method and order of administration of the constituents may vary according to the particular pharmaceutical formulation of the 2-pyrrolino-13-deoxyanthracycline of formula X and the particular pharmaceutical formulation of the 13-deoxyanthracycline of formula Y being utilized, the particular cancer or cell proliferative disorder being treated, the severity of the disease state being treated, and the particular patient being treated. The dosage ranges for the administration of the constituents may vary with the age, condition, sex, and extent of the disease in the patient, and can be determined by one of ordinary skill in the art.

A pharmaceutical composition of the present disclosure comprises a 2-pyrrolino-13-deoxyanthracycline of formula X; pharmaceutically acceptable salt thereof, deuterated form thereof, prodrug thereof, isomer thereof, and/or solvate thereof mixed together with a 13-deoxy anthracycline of formula Y; pharmaceutically acceptable salt thereof, deuterated form thereof, prodrug thereof, isomer thereof, and/or solvate thereof in a pharmaceutically acceptable carrier or excipient. These pharmaceutical compositions of the present disclosure are useful in anticancer therapy and the treatment of cell proliferative disorders.

The pharmaceutically acceptable carriers or excipients are well known to those having ordinary skill in the art of formulating compounds in a form of pharmaceutical compositions, combinations, mixtures, and preparations. A pharmaceutically acceptable carrier refers to one or more compatible solid or liquid filler, diluent, or encapsulating substances which are suitable for administration to mammals including humans. Pharmaceutical compositions, combinations, mixtures, and preparations suitable for parenteral administration are formulated in a sterile form which may be a sterile solution or suspension in an acceptable diluent or solvent.

The amount of an active ingredient contained in the pharmaceutical composition may vary quite widely depending on many factors, such as the route of administration and the vehicle. In the present invention, a pharmaceutical composition may contain from about 0.1 to 1000 mg of a 2-pyrrolino-13-deoxyanthracycline of formula X; pharmaceutically acceptable salt thereof, deuterated form thereof, prodrug thereof, isomer thereof, and/or solvate thereof and from about 0.1 to 1000 mg of a 13-deoxyanthracycline of formula Y; pharmaceutically acceptable salt thereof, deuterated form thereof, prodrug thereof, isomer thereof, and/or solvate thereof.

In the method of the subject disclosure, a 2-pyrrolino-13-deoxyanthracycline of formula X; pharmaceutically acceptable salt thereof, deuterated form thereof, prodrug thereof, isomer thereof, and/or solvate thereof is administered to a patient in need thereof at a dose from about 0.1 mg/m$^2$ body surface area to about 1000 mg/m$^2$ body surface area, more typically from about 10 mg/m$^2$ body surface area to about 500 mg/m$^2$ body surface area, and more typically by the parenteral route of administration. The 13-deoxy anthracycline of formula Y; pharmaceutically acceptable salt thereof, deuterated form thereof, prodrug thereof, isomer thereof, and/or solvate thereof of the present disclosure is administered to a patient in need thereof at a dose from about 0.1 mg/m$^2$ to about 1000 mg/m$^2$, more typically from about 10 mg/m$^2$ to about 500 mg/m$^2$, and more typically by the parenteral route of administration. The 2-pyrrolino-13-deoxyanthracycline and the 13-deoxyanthracycline can be administered together, in a single composition, combination, mixture, or preparation, or can be administered separately in either order, sequentially in either order, or consecutively in either order. When not administered together, the second compound is typically administered within 72 hours of administering the first compound.

The anticancer/antiproliferative therapeutic effects of the 2-pyrrolino-13-deoxyanthracycline are significantly increased by the 13-deoxy anthracycline without an increase in toxicity. Likewise, the anticancer/antiproliferative therapeutic effects of the 13-deoxyanthracycline are significantly increased by the 2-pyrrolino-13-deoxyanthracycline without an increase in toxicity. This lack of increase in toxicity is due, in part, to the synergism between the two types of compounds. The doses of the 2-pyrrolino-13-deoxyanthracycline and the 13-deoxy anthracycline can be administered as frequently as necessary. The actual method and order of administration will vary according to the particular formulation, composition, combination, mixture, or preparation, the particular cancer being treated, and the particular patient being treated.

The enhanced anti-cell proliferative action of a combination of a 2-pyrrolino-13-deoxy anthracycline of formula X with a 13-deoxy anthracycline of formula Y of the present disclosure is shown, by way of example, in the following biological test, which is intended to illustrate but not to limit the present invention.

Example 4

A fibrosarcoma cell line, HT1080, was used to measure the IC$_{50}$'s and IC$_{10}$'s (the inhibitory concentration of a compound required to inhibit cell growth by 10%) of Compound IV and Compound III, as described in Example 2. An IC$_{50}$ concentration represents a therapeutic amount of compound. An IC$_{10}$ represents a non-therapeutic sub-effective amount of a compound. The cells were passaged and seeded at 5,000 cells/well on 96-well plates and the plates were incubated for 24 hours. After incubation, the media was changed and the IC$_{50}$'s and IC$_{10}$'s of compound IV and compound III were measured after 48 hours of incubation. Then, the IC$_{50}$'s of compound IV in the presence of compound III at an IC$_{10}$ concentration and of compound III in the presence of compound IV at an IC$_{10}$ concentration were measured after 48 hours of incubation. After the incubations, 20 μM of 0.1% AlamarBlue in 1×PBS was added to each well. The plates were then incubated for a final 24 h. The plates were read on a microplate reader with an ex/em of 485/528.

TABLE 4

IC$_{50}$'s and IC$_{10}$'s (micromolar) of compound IV and Compound III, the IC$_{50}$ of compound IV in the presence of an IC$_{10}$ of compound III, and the IC$_{50}$ of compound III in the presence of an IC$_{10}$ of compound IV, in HT1080 cells.

|  | Compound IV | Compound III | Compound IV plus IC$_{10}$ of III | Compound III plus IC$_{10}$ of IV |
|---|---|---|---|---|
| IC$_{50}$ | 12.53 | 63.7 | 1.01 | 1.78 |
| IC$_{10}$ | 0.84 | 5.34 | — | — |

Compound IV is 12 times (12.5/1.01) more potent in the presence of a nontherapeutic amount of compound III and compound III is 35 times (63.7/1.78) more potent in the presence of a nontherapeutic amount of compound IV. These results provide clear evidence that compounds IV and III are synergistic with each other. This result is unexpected because both compounds are anthracyclines and are expected to work by the same mechanism and, therefore, be only additive when combined. That is, one of ordinary skill in the art would expect the IC$_{10}$ concentrations of one compound to have a little or no effect on the potency of the other compound. Thus, the combination of a 2-pyrrolino-13-deoxy anthracyclines of formula X with 13-deoxyanthracyclines of formula Y provide an improved composition with increased potency and efficacy over the compounds used by themselves.

A synergistic interaction occurs when the pharmacologic effect of the administration of the combination of two drugs is greater than the additive effects of the two drugs administered separately. For example, assume the dose of a first drug to produce a 30% response is 100 units and the dose of a second drug to produce a 30% response is 10 units. If 100 units of the first drug plus 10 units of the second drug produce a 60% response, then there is an additive effect between the two drugs. However, if 100 units of the first drug plus 10 units of the second drug produce a 90% response, then there is a synergistic or supra-additive effect between the two drugs. If the compounds interacted in an additive way, one would expect the IC$_{50}$ of compound IV to decrease from 12.53 micromolar to 10 micromolar in the presence of compound III at an IC$_{10}$ concentration. However, the IC$_{50}$ of compound IV decreased to 1 micromolar. Similarly, one would expect the IC$_{50}$ of compound III to decrease from 63.37 micromolar to 50 micromolar in the presence of compound IV at an IC$_{10}$ concentration. However, the IC$_{50}$ of compound III decreased to 1.78 micromolar. Thus, 2-pyrrolino-13-deoxy anthracyclines of formula X and 13-deoxyanthracyclines of formula Y of the present disclosure act in an enhanced manner or synergistically with each other to produce highly potent and effective compositions, combinations, mixtures or preparations for suppressing the growth of cancer cells.

In keeping with the present disclosure, the compounds of the present disclosure can be used alone or in appropriate association, and also may be used in combination with pharmaceutically acceptable carriers and other pharmaceutically active compounds. The active agent may be present in the pharmaceutical composition in any suitable quantity.

The pharmaceutically acceptable carriers described herein, for example, vehicles, adjuvants, excipients, or diluents, are well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices.

The choice of carrier will be determined in part by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, intraperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granule; (c) powders; (d) suspensions in an appropriate liquid; and (e) suitable emulsions. Liquid formulations may include diluents, such as water, cyclodextrin, dimethyl sulfoxide and alcohols, for example, ethanol, benzyl alcohol, propylene glycol, glycerin, and the polyethylene alcohols including polyethylene glycol, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, the addition to the active ingredient in an inert base, such as gelatin and glycerin, or sucrose and acadia, emulsions, and gels containing, in addition to the active ingredient, such carriers as are known in the art.

The compounds alone or in combination with other suitable components, can be made into aerosol formulations to be administered via inhalation. These aerosol formulations can be placed into pressurized acceptable propellants, such as dichlorodifluoromethane, propane, and nitrogen. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1, 3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcelluslose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example. dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl ß-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present disclosure. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The formulations can be presented in unit-does or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutical carriers for injectable compositions are well known to those of ordinary skill in the art. See *Pharmaceutics and Pharmacy Practice*, J.B. Lippincott Co., Philadelphia, Pa., Banker and Chalmers, Eds., 238-250 (1982) and *ASHP Handbook on Injectable Drugs*, Toissel, 4$^{th}$ ed., 622-630 (1986).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, and gels containing, in addition to the active ingredient, such carriers as are known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

One skilled in the art will appreciate that suitable methods of exogenously administering a compound of the present disclosure to an animal are available, and, although more than one route can be used to administer a particular compound, a particular route can provide a more immediate and more effective reaction than another route.

Exemplary embodiments of the present disclosure include:

Embodiment A

A compound represented by the formula:

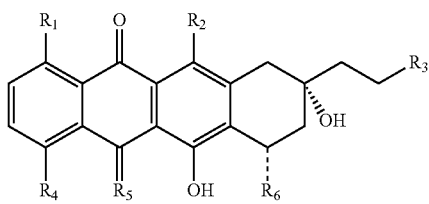

wherein:
each $R_1$, $R_2$, and $R_3$ individually is H or OH;
$R_4$ is selected from the group consisting of H, OH, alkyl, and O-alkyl;
$R_5$ is O or NH; and
$R_6$ is 2-pyrrolino-daunosamine or 2-pyrrolino-epi-daunosamine;
pharmaceutically acceptable salts thereof, deuterated form thereof, prodrug thereof, isomer thereof, solvate thereof, and mixtures thereof.

Embodiment B

The compound of embodiment A, wherein said compound is a derivative of an anthracycline selected from the group consisting of 2-pyrrolino-13-deoxydoxorubicin, 2-pyrrolino-13-deoxydaunorubicin, 2-pyrrolino-13-deoxyepirubicin, 2-pyrrolino-13-deoxycarminomycin, and 2-pyrrolino-13-deoxyidarubicin and the 5-imino analogs thereof.

Embodiment C

A pharmaceutical composition comprising the compound of embodiment A or B, and a pharmaceutically acceptable carrier or excipient.

Embodiment D

A method for suppressing the growth of cells, comprising administering to a mammal in need thereof a therapeutically effective amount of a compound comprising: a 2-pyrrolino-13-deoxy anthracycline, having the formula:

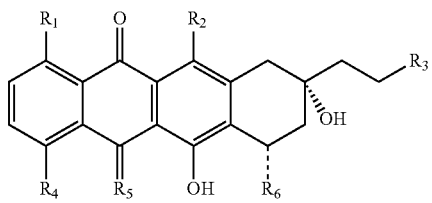

wherein:
each $R_1$, $R_2$, and $R_3$ individually is H or OH;
$R_4$ is selected from the group consisting of H, OH, alkyl, and O-alkyl;
$R_5$ is O or NH; and
$R_6$ is 2-pyrrolino-daunosamine or 2-pyrrolino-epi-daunosamine,
pharmaceutically acceptable salt thereof, deuterated form thereof, prodrug thereof, isomer thereof, solvate thereof, and mixtures thereof.

Embodiment E

The method of embodiment D, wherein said compound is a derivative of an anthracycline selected from the group consisting of 2-pyrrolino-13-deoxydoxorubicin, 2-pyrrolino-13-deoxydaunorubicin, 2-pyrrolino-13-deoxyepirubicin, 2-pyrrolino-13-deoxycarminomycin, and 2-pyrrolino-13-deoxyidarubicin and the 5-imino analogs thereof.

Embodiment F

A therapeutically effective amount of a synergistic combined preparation comprising a first compound and a second compound, wherein: the first compound is a 2-pyrrolino-13-deoxyanthracycline, having the formula:

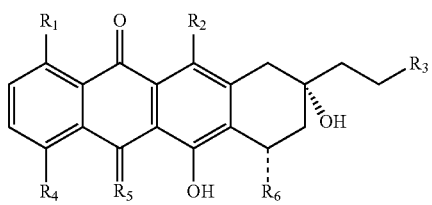

wherein:

each $R_1$, $R_2$, and $R_3$ individually is H or OH;

$R_4$ is selected from the group consisting of H, OH, alkyl, and O-alkyl;

$R_5$ is O or NH; and $R_6$ is 2-pyrrolino-daunosamine or 2-pyrrolino-epi-daunosamine; pharmaceutically acceptable salt thereof, deuterated form thereof, prodrug thereof, isomer thereof, solvate thereof, and mixtures thereof; and the second compound is a 13-deoxyanthracycline having the formula:

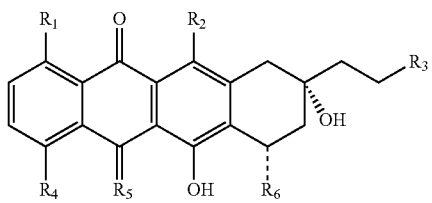

wherein
each of $R_1$, $R_2$ and $R_3$ is independently selected from the group consisting of H and OH;

$R_4$ is selected from the group consisting of H, OH, alkyl, and O-alkyl;

$R_5$ is selected from the group consisting of O and NH; and $R_6$ is a sugar moiety; pharmaceutically acceptable salt thereof, deuterated form thereof, prodrug thereof, isomer thereof, solvate thereof, and mixtures thereof; and wherein said therapeutically effective amount suppresses the growth of cells.

Embodiment G

The synergistic combined preparation of embodiment F, wherein said first compound is a derivative of an anthracycline selected from the group consisting of 2-pyrrolino-13-deoxydoxorubicin, 2-pyrrolino-13-deoxydaunorubicin, 2-pyrrolino-13-deoxyepirubicin, 2-pyrrolino-13-deoxycarminomycin, and 2-pyrrolino-13-deoxyidarubicin and the 5-imino analogs thereof and said second compound is a derivative of an anthracycline selected from the group consisting of 13-deoxydoxorubicin, 13-deoxydaunorubicin, 13-deoxyepirubicin, 13-deoxycarminomycin, 13-deoxyidarubicin, 13-deoxyannamycin, and 13-deoxyamrubicin and the 5-imino analogs thereof.

Embodiment H

A pharmaceutical composition comprising the synergistic combined preparation of Embodiment F or G, and a pharmaceutically acceptable carrier or excipient.

Embodiment I

A method for suppressing the growth of cells with a synergistic combined preparation of a first compound and a second compound, comprising administering to a mammal in need thereof a therapeutically effective amount of said synergistic combined preparation, said first compound being a 2-pyrrolino-13-deoxyanthracycline having the formula:

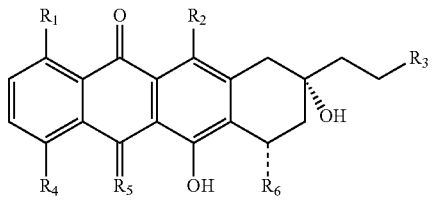

wherein:

each $R_1$, $R_2$, and $R_3$ individually is H or OH;

$R_4$ is selected from the group consisting of H, OH, alkyl, and O-alkyl;

$R_5$ is O or NH; and $R_6$ is 2-pyrrolino-daunosamine or 2-pyrrolino-epi-daunosamine; pharmaceutically acceptable salt thereof, deuterated forms thereof, prodrug thereof, isomer thereof, solvate thereof, and mixtures thereof; and said second compound being a 13-deoxyanthracycline having the formula:

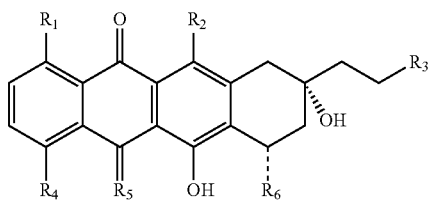

wherein
each of $R_1$, $R_2$ and $R_3$ is independently selected from the group consisting of H and OH;

$R_4$ is selected from the group consisting of H, OH, alkyl, and O-alkyl;

$R_5$ is selected from the group consisting of O and NH; and $R_6$ is a sugar moiety; pharmaceutically acceptable salt thereof, deuterated form thereof, prodrug thereof, isomer thereof, solvate thereof, and mixtures thereof; and wherein said therapeutically effective amount suppresses the growth of cells.

Embodiment J

The method of embodiment I, wherein said first compound is a derivative of an anthracycline selected from the group consisting of 2-pyrrolino-13-deoxydoxorubicin, 2-pyrrolino-13-deoxydaunorubicin, 2-pyrrolino-13-deoxyepirubicin, 2-pyrrolino-13-deoxycarminomycin, and 2-pyrrolino-13-deoxyidarubicin and the 5-imino analogs thereof and the second compound is a derivative of an anthracycline selected from the group consisting of 13-deoxydoxorubicin, 13-deoxydaunorubicin, 13-deoxyepirubicin, 13-deoxycarminomycin, 13-deoxyidarubicin, 13-deoxyannamycin, and 13-deoxyamrubicin and the 5-imino analogs thereof.

Embodiment K

The synergistic combined preparation of embodiment F or G wherein said second compound is present in an amount that is lower than its therapeutically effective amount.

Embodiment L

The synergistic combined preparation of embodiment K, wherein the weight ratio of the second compound to the first component is about 0.005 to about 0.10:1.

Embodiment M

The synergistic combined preparation of embodiment K, wherein the weight ratio of the second compound to the first component is about 0.01 to about 0.10:1.

Embodiment N

The synergistic combined preparation of embodiment F or G wherein said first compound is present in an amount that is lower than its therapeutically effective amount.

Embodiment O

The synergistic combined preparation of embodiment N, wherein the weight ratio of the first compound to the second component is about 0.005 to about 0.10:1.

Embodiment P

The synergistic combined preparation of embodiment N, wherein the weight ratio of the first compound to the second component is about 0.01 to about 0.10:1.

Embodiment Q

The method of embodiment I or J wherein said second compound is administered in an amount that is lower than its therapeutically effective amount.

Embodiment R

The method of embodiment Q, wherein the weight ratio of the second compound to the first component is about 0.005 to about 0.10:1.

Embodiment S

The method of embodiment Q, wherein the weight ratio of the second compound to the first component is about 0.01 to about 0.10:1.

Embodiment T

The method of embodiment I or J wherein said second compound is administered in an amount that is lower than its therapeutically effective amount.

Embodiment U

The method of embodiment T, wherein the weight ratio of the first compound to the second component is about 0.005 to about 0.10:1.

Embodiment V

The method of embodiment Q, wherein the weight ratio of the first compound to the second component is about 0.01 to about 0.10:1.

The term "comprising" (and its grammatical variations) as used herein is used in the inclusive sense of "having" or "including" and not in the exclusive sense of "consisting only of" The terms "a", "an" and "the" as used herein are understood to encompass the plural as well as the singular, unless indicated otherwise.

The foregoing description illustrates and describes the disclosure. Additionally, the disclosure shows and describes only the preferred embodiments but, as mentioned above, it is to be understood that the preferred embodiments are capable of being formed in various other combinations, modifications, and environments and are capable of changes or modifications within the scope of the invention concepts as expressed herein, commensurate with the above teachings and/or the skill or knowledge of the relevant art. The embodiments described herein above are further intended to explain the best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended that the appended claims be construed to include alternative embodiments.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A compound represented by the formula: wherein:

each $R_1$, $R_2$, and $R_3$ individually is H or OH;
$R_4$ is selected from the group consisting of H, OH, alkyl, and O-alkyl;
$R_5$ is O or NH; and
$R_6$ is 2-pyrrolino-daunosamine or 2-pyrrolino-epi-daunosamine; a pharmaceutically acceptable salt thereof, deuterated form thereof, isomer thereof, solvate thereof, and mixture thereof.

2. The compound of claim 1, wherein said compound is a derivative of an anthracycline selected from the group consisting of 2-pyrrolino-13-deoxydoxorubicin, 2-pyrrolino-13-deoxydaunorubicin, 2-pyrrolino-13-deoxyepirubicin, 2-pyrrolino-13-deoxycarminomycin, and 2-pyrrolino-13-deoxyidarubicin and the 5-imino analogs thereof.

3. A pharmaceutical composition comprising the compound of claim 1, and a pharmaceutically acceptable carrier or excipient.

4. A pharmaceutical composition comprising the compound of claim 2, and a pharmaceutically acceptable carrier or excipient.

5. A method for suppressing the growth of cells, comprising administering to a mammal in need thereof a therapeutically effective amount of a compound comprising:

a 2-pyrrolino-13-deoxy anthracycline, or pharmaceutically acceptable salts thereof, said 2-pyrrolino-13-deoxy anthracycline having the formula:

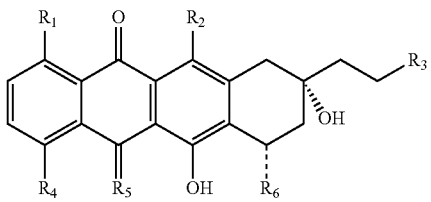

wherein:
each $R_1$, $R_2$, and $R_3$ individually is H or OH;
$R_4$ is selected from the group consisting of H, OH, alkyl, and O-alkyl;
$R_5$ is O or NH; and
$R_6$ is 2-pyrrolino-daunosamine or 2-pyrrolino-epi-daunosamine;
pharmaceutically acceptable salt thereof, deuterated form thereof, isomer thereof, solvate thereof, and mixture thereof.

6. The method of claim 5, wherein said compound is a derivative of an anthracycline selected from the group consisting of 2-pyrrolino-13-deoxydoxorubicin, 2-pyrrolino-13-deoxydaunorubicin, 2-pyrrolino-13-deoxyepirubicin, 2-pyrrolino-13-deoxycarminomycin, and 2-pyrrolino-13-deoxyidarubicin and the 5-imino analogs thereof.

7. A therapeutically effective amount of a synergistic combined preparation comprising a first compound and a second compound, wherein: the first compound is a 2-pyrrolino-13-deoxyanthracycline having the formula:

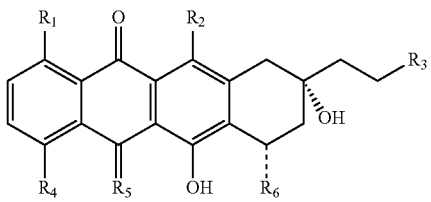

wherein:
each $R_1$, $R_2$, and $R_3$ individually is H or OH;
$R_4$ is selected from the group consisting of H, OH, alkyl, and O-alkyl;
$R_5$ is O or NH; and
$R_6$ is 2-pyrrolino-daunosamine or 2-pyrrolino-epi-daunosamine; pharmaceutically acceptable salt thereof, deuterated form thereof, isomer thereof, solvate thereof, and mixture thereof and
the second compound is a 13-deoxyanthracycline having the formula:

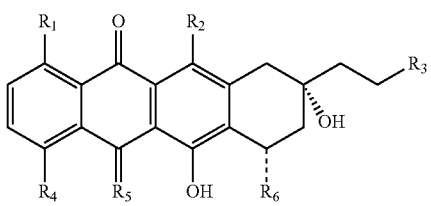

wherein
each of $R_1$, $R_2$ and $R_3$ is independently selected from the group consisting of H and OH;
$R_4$ is selected from the group consisting of H, OH, alkyl, and O-alkyl;
$R_5$ is selected from the group consisting of 0 and NH; and
$R_6$ is a sugar moiety; pharmaceutically acceptable salt thereof, deuterated form thereof, isomer thereof, solvate thereof, and mixture thereof and
wherein said therapeutically effective amount suppresses the growth of cells.

8. The synergistic combined preparation of claim 7, wherein said first compound is a derivative of an anthracycline selected from the group consisting of 2-pyrrolino-13-deoxydoxorubicin, 2-pyrrolino-13-deoxydaunorubicin, 2-pyrrolino-13-deoxyepirubicin, 2-pyrrolino-13-deoxycarminomycin, and 2-pyrrolino-13-deoxyidarubicin; pharmaceutically acceptable salt thereof, deuterated form thereof, isomer thereof, solvate thereof, and mixtures thereof and the 5-imino analogs thereof and said second compound is a derivative of an anthracycline selected from the group consisting of 13-deoxydoxorubicin, 13-deoxydaunorubicin, 13-deoxyepirubicin, 13-deoxycarminomycin, 13-deoxyidarubicin, 13-deoxyannamycin, and 13-deoxyamrubicin and the 5-imino analogs thereof; pharmaceutically acceptable salt thereof, deuterated form thereof, isomer thereof, solvate thereof, and mixtures thereof.

9. A pharmaceutical composition comprising the synergistic combined preparation of claim 7, and a pharmaceutically acceptable carrier or excipient.

10. A pharmaceutical composition comprising the synergistic combined preparation of claim 8, and a pharmaceutically acceptable carrier or excipient.

11. The synergistic combined preparation of claim 7 wherein said second compound is present in an amount that is lower than its therapeutically effective amount.

12. The synergistic combined preparation of claim 11 wherein the weight ratio of the second compound to the first component is about 0.005 to about 0.10:1.

13. The synergistic combined preparation of claim 7 wherein said first compound is present in an amount that is lower than its therapeutically effective amount.

14. The synergistic combined preparation of claim 13 wherein the weight ratio of the first compound to the second component is about 0.005 to about 0.10:1.

15. A method for suppressing the growth of cells with a synergistic combined preparation of a first compound and a second compound, comprising administering to a mammal in need thereof a therapeutically effective amount of said synergistic combined preparation, said first compound being a 2-pyrrolino-13-deoxyanthracycline having the formula:

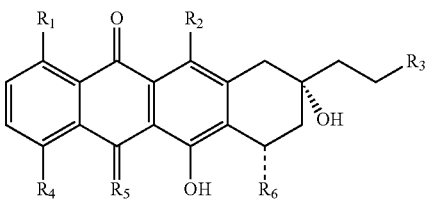

wherein:
each $R_1$, $R_2$, and $R_3$ individually is H or OH;
$R_4$ is selected from the group consisting of H, OH, alkyl, and O-alkyl;

$R_5$ is O or NH; and $R_6$ is 2-pyrrolino-daunosamine or 2-pyrrolino-epi-daunosamine; pharmaceutically acceptable salt thereof, deuterated form thereof, isomer thereof, solvate thereof, and mixture thereof, and said second compound being a 13-deoxyanthracycline having the formula:

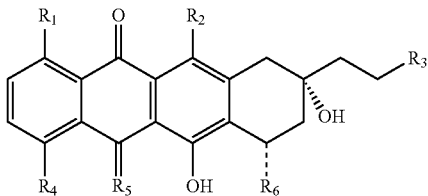

wherein each of $R_1$, $R_2$ and $R_3$ is independently selected from the group consisting of H and OH;

$R_4$ is selected from the group consisting of H, OH, alkyl, and O-alkyl;

$R_5$ is selected from the group consisting of O and NH; and $R_6$ is a sugar moiety; pharmaceutically acceptable salt thereof, deuterated form thereof, isomer thereof, solvate thereof, and mixture thereof and wherein said therapeutically effective amount suppresses the growth of cells.

16. The method of claim 15, wherein said first compound is a derivative of an anthracycline selected from the group consisting of 2-pyrrolino-13-deoxydoxorubicin, 2-pyrrolino-13-deoxydaunorubicin, 2-pyrrolino-13-deoxyepirubicin, 2-pyrrolino-13-deoxycarminomycin, and 2-pyrrolino-13-deoxyidarubicin and the 5-imino analogs thereof; pharmaceutically acceptable salts thereof, deuterated form thereof, isomer thereof, solvate thereof, and mixtures thereof and the second compound is a derivative of an anthracycline selected from the group consisting of 13-deoxydoxorubicin, 13-deoxydaunorubicin, 13-deoxyepirubicin, 13-deoxycarminomycin, 13-deoxyidarubicin, 13-deoxyannamycin, and 13-deoxyamrubicin and the 5-imino analogs thereof; pharmaceutically acceptable salt thereof, deuterated form thereof, isomer thereof, solvate thereof, and mixtures thereof.

17. The method of claim 15 wherein said second compound is administered in an amount that is lower than its therapeutically effective amount.

18. The method of claim 17 wherein the weight ratio of the second compound to the first component is about 0.005 to about 0.10:1.

19. The method of claim 15 wherein said second compound is administered in an amount that is lower than its therapeutically effective amount.

20. The method of claim 19 wherein the weight ratio of the first compound to the second component is about 0.005 to about 0.10:1.

* * * * *